(12) United States Patent
Loeb et al.

(10) Patent No.: US 6,802,838 B2
(45) Date of Patent: Oct. 12, 2004

(54) DEVICES AND METHODS FOR DIRECTED, INTERSTITIAL ABLATION OF TISSUE

(75) Inventors: Marvin P. Loeb, Huntington Beach, CA (US); L. Dean Crawford, Irvine, CA (US); James W. Pergl, Lake Forest, CA (US); Randy P. Graham, Irvine, CA (US)

(73) Assignee: Trimedyne, Inc., Irvine, CA (US)

( * ) Notice: Subject to any disclaimer, the term of this patent is extended or adjusted under 35 U.S.C. 154(b) by 96 days.

(21) Appl. No.: 10/127,382

(22) Filed: Apr. 22, 2002

(65) Prior Publication Data

US 2003/0199860 A1 Oct. 23, 2003

(51) Int. Cl.$^7$ ............................................... A61B 18/20
(52) U.S. Cl. ........................................ 606/13; 606/15
(58) Field of Search .............................. 606/13, 14, 15, 606/16; 607/88, 89

(56) References Cited

U.S. PATENT DOCUMENTS 5,246,436 A * 9/1993 Rowe ........................... 606/13

* cited by examiner

Primary Examiner—Michael Peffley
Assistant Examiner—Aaron Roane
(74) Attorney, Agent, or Firm—Olson & Hierl, Ltd.

(57) ABSTRACT

The invention relates to a catheter device including an optical fiber whose distal end is disposed within a hollow tube with a sharp or syringe shaped distal end, which may be inserted into tissue. The distal end of the optical fiber and the hollow tube are configured so as to emit, by refraction (total internal reflection) or reflection from a metal surface, laser energy at an angle of about 80° to about 90° relative to the longitudinal axis of the optical fiber and hollow tube. A first fluid channel within the distal end portion of the tube enables fluid to be infused to cool the distal end of the tube and to cool and clean the emission face of the optical fiber. A second, relatively larger diameter fluid channel in the tube enables the fluid, flowing through said first channel along with hot gasses from the vaporization of tissue, to exit the device through a second port in the tube, away from the tissue being treated. A vacuum can be applied to the second fluid channel to more effectively remove the infused, cooling fluid and hot gasses from the tissue being treated. Alternatively, the tube can incorporate a distal end portion which can be articulated to allow the insertion of the device into tissue perpendicular to the tissue's surface, from which laser energy can be emitted forwardly.

15 Claims, 9 Drawing Sheets

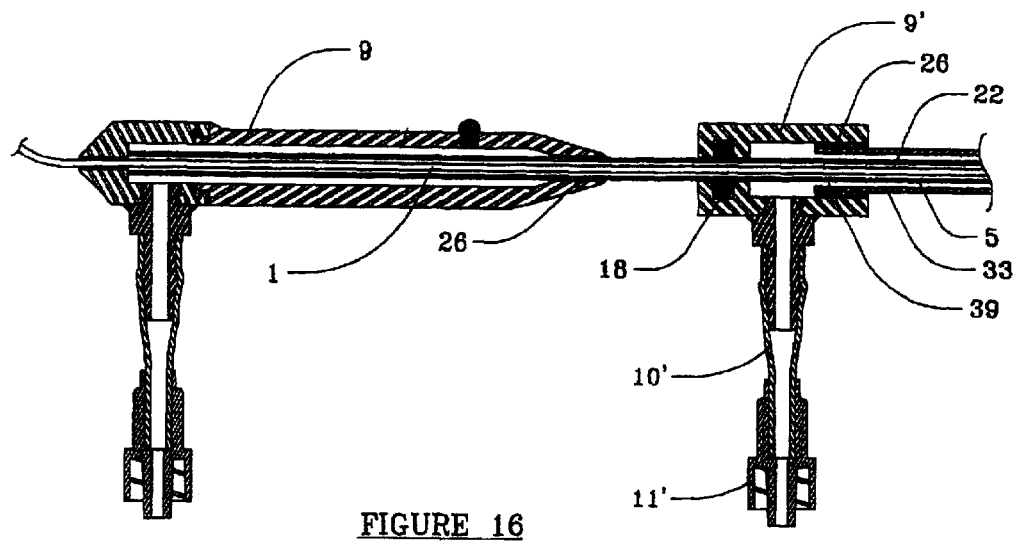
FIGURE 16
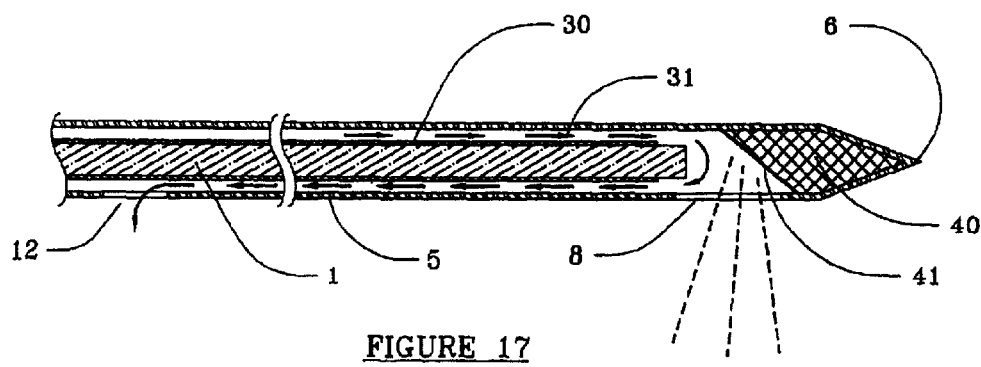
FIGURE 17
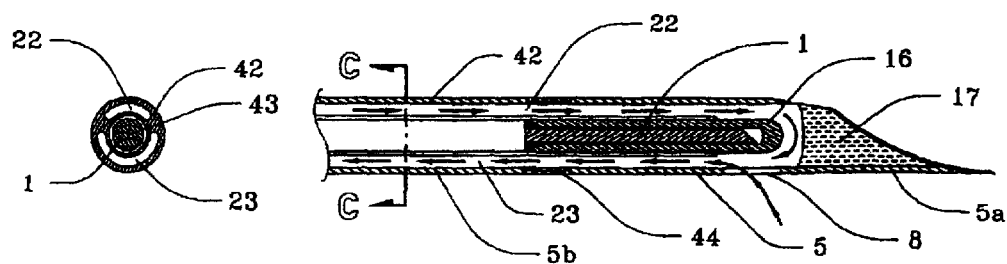
FIGURE 18
FIGURE 19

DEVICES AND METHODS FOR DIRECTED, INTERSTITIAL ABLATION OF TISSUE

FIELD OF THE INVENTION

The invention entails devices and methods for selectively vaporizing unwanted body tissues, such as excess tissue in the male prostate gland or a tumor, without damaging adjoining tissues.

BACKGROUND OF THE INVENTION

Benign prostatic hyperplasia or "BPH", commonly referred to as an enlarged prostate, affects more than 50% of men over age 55 and is a worldwide problem. Approximately 200,000 surgeries to treat this condition are presently performed each year in the United States at a cost estimated at $1.6 billion annually. While pharmaceuticals, such as terazosin, may limit prostate growth for a period of time, eventually a surgical solution may be required.

The long standing surgical procedure for treating BPH is transurethral resection of the prostate or TURP, in which an electrosurgical loop heated by radiofrequency ("RF") energy is moved to and fro within the prostate to resect (cut out) troughs of prostate tissue. While a TURP produces satisfactory voiding of urine, it requires general anesthesia and an hour or more of costly operating room time and entails up to 15% impotence, 5–10% permanent incontinence and bleeding requiring a transfusion in up to 10% of the patients. In addition, most TURP patients suffer from retrograde ejaculation, and up to 30% or more of TURP patients experience an infection or other adverse effect.

Recently, high powered RF roller ball devices have been introduced, which have somewhat reduced the bleeding and other adverse effects of a TURP. However, the use of RF roller ball devices requires general anesthesia and an hour or more of costly operating room time. Holmium lasers can be used for resection of the prostate, producing urine flow results equal to a TURP, while eliminating bleeding and most of the other adverse effects of the above described procedures using RF energy. However, Holmium laser resection typically requires one hour or more of expensive operating room time and general anesthesia.

The interstitial (within tissue) use of microwave, laser or RF energy to thermally coagulate a portion of the prostate, while taking less time and avoiding general anesthesia, does not significantly reduce the prostate's volume and thus produces less urine voiding relief than a TURP, high power RF roller ball or Holmium laser resection procedure. In addition, the patients treated with interstitial coagulating devices experience dysuria and discomfort for weeks after the procedure. If the tissue immediately underlying the urethra, which constitutes the exterior surface of the lobes of the prostate, is coagulated, the urethra dies, due to loss of its blood supply, leaving an open, irritating wound. The coagulated tissue then sloughs off and is excreted in the urine over a period of 3–6 weeks.

It would be desirable to be able to remove a sufficient amount of prostate tissue to provide immediate voiding and relief of BPH symptoms, while protecting the urethra and the immediately underlying tissue from damage, in a short, outpatient procedure, preferably in an outpatient treatment facility or a physician's office under local anesthesia and/or sedation.

Laser or RF energy can be used to coagulate a tumor, but coagulation occurs irregularly, as conduction of heat through tissue of differing densities and water content is not uniform. Consequently, it is necessary to closely observe the coagulation procedure to avoid damaging nearby blood vessels, nerves and other vital tissues. While a vaporization zone can be distinguished from normal tissue by ultrasound imaging, coagulated tissue cannot be differentiated from normal tissue by ultrasound imaging. As a result, expensive magnetic resonance imaging (MRI) equipment would be required to visually monitor the coagulation procedure, so that the process can be halted if the coagulation zone approaches important blood vessels, ducts, nerves or other tissues. Unhappily, the use of MRI equipment would increase the cost of an already expensive procedure.

It would be desirable to be able to accurately vaporize a tumor of any shape, while directing laser energy away from a vital blood vessel, duct, nerve or other tissue adjoining the tumor, with the ability to observe the vaporization process using a less costly ultrasound imaging system.

SUMMARY OF THE INVENTION

The present invention provides for the vaporization of unwanted tissue in a mammalian body, without producing excessive coagulation of surrounding tissues and avoiding thermal damage to a nearby mucosal surface or an adjacent, important blood vessel, duct, nerve or other structure.

This is achieved by a catheter device adapted to deliver energy from a laser source to a body tissue, which device includes an elongate, sharp-ended hollow tube having first and second ports spaced from one another, a flexible energy conduit, adapted for connection to a laser source at its proximal end, a fluid conduit for passing a fluid through said ports for cooling and cleaning the distal end of the energy conduit, and a separate conduit for withdrawing fluid and hot gasses from the vaporization of tissue into the hollow tube.

The fluid can be passed through the ports by positive pressure, and gasses can be withdrawn by vacuum, i.e., negative pressure. The distal end of the flexible energy conduit is adapted to emit energy to a predetermined tissue site so as to ablate or vaporize the tissue.

In one embodiment of the device embodying the present invention, energy, such as laser energy, is transmitted through an optical fiber, whose distal radial end is beveled at an angle about 30° to about 50°, preferably about 39° to about 40°, into a prism-like shape, encased within a quartz or fused silica capillary tube and disposed within a metal tube with a sharp distal end, such as a syringe needle. Encasing the optical fiber in a capillary tube provides a significant difference in refractive index (air at 1.0 versus quartz or fused silica at about 1.33) at the beveled surface, which enables total internal reflection of emitted energy. As a result, energy is emitted from a port in the metal tube at an angle of approximately 80° to about 90° transverse to the axis of the optical fiber.

Two unique fluid channels and ports in the tube enable fluid to be infused through one channel in the metal tube to cool the distal end portion of the optical fiber as well as the internal face of the distal end of the metal tube, cool and clean the distal closed end face of the capillary tube from which the energy is emitted. Negative pressure applied through the other channel in the tube may also be used to evacuate the cooling fluid and the hot gasses from the vaporization of tissue, avoiding the excess coagulation of tissue surrounding the target area by thermal conduction.

An outer sheath of fluorinated hydrocarbon such as Teflon®, a product of DuPont de Nemours of Wilmington, Del., other plastic material, or a ceramic may be employed around the sheath containing the optical fiber to facilitate penetration of tissue, prevent tissue adherence and provide insulation to avoid thermal damage to tissue from heat conducted along the needle.

In use, the present device is inserted into tissue and oriented to emit laser energy in a desired pattern, away from a region or tissue to be preserved, such as the mucosa or endothelial surface of an organ or an important blood vessel, duct, nerve or other structure, to prevent thermal damage thereto. The device can be rotated in an arc while lasing, or advanced and/or withdrawn while lasing, or both. Such a device, for example, could be used to vaporize a portion of the lobes of the prostate, without damaging the sensitive urethra, or its immediately underlying, supportive tissue, or to vaporize a tumor, without damaging surrounding normal tissue or a nearby major blood vessel, duct, nerve or other structure.

BRIEF DESCRIPTION OF THE DRAWINGS

FIG. 16 is an enlarged, partial, cross-sectional view of yet another device embodying the present invention similar to that shown in FIG. 14 but with a different fluid flow pattern;

FIG. 17 is an enlarged, partial, cross-sectional, side elevational view of another alternate embodiment of the device of FIG. 1;

FIG. 18 is a cross sectional view of an alternate catheter insert embodiment taken along plane C—C in FIG. 19;

FIG. 19 is an enlarged, partial, cross-sectional, side elevational view of the distal end of the device of FIG. 1 incorporating the catheter insert embodiment of FIG. 18;

DESCRIPTION OF THE PREFERRED EMBODIMENTS OF THE INVENTION

Figure 1:
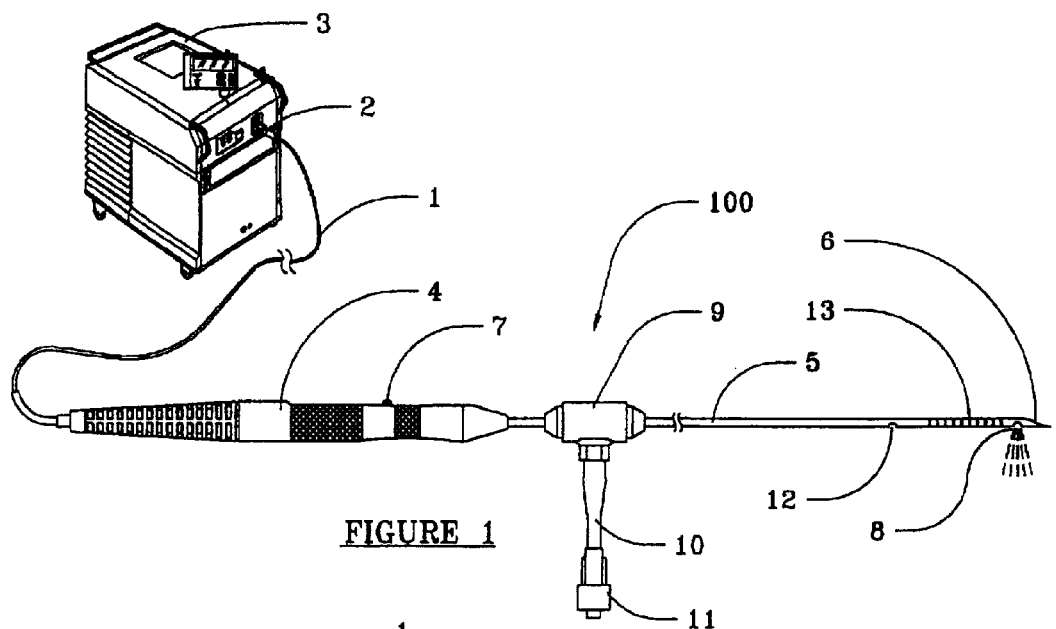
FIG. 1 is a side elevational view of a device of the present invention.

While this invention is susceptible of embodiment in many different forms, specific embodiments are shown in the drawings and are described herein in detail, with the understanding that the present disclosure is to be considered as an exemplification of the principles of the invention and is not to be limited to the specific embodiments illustrated.

An apparatus aspect of the present invention is a medical catheter device for delivering localized energy to a tissue in a patient's body in an amount sufficient to ablate or vaporize the tissue. In use, the catheter device is suitably positioned within a patient's body by insertion through a body lumen, cavity or surgically created passageway, and advanced to a predetermined site within the body. The device of the present invention is particularly suited for the vaporization of prostate tissue and involves the use of laser energy.

Figure 2:
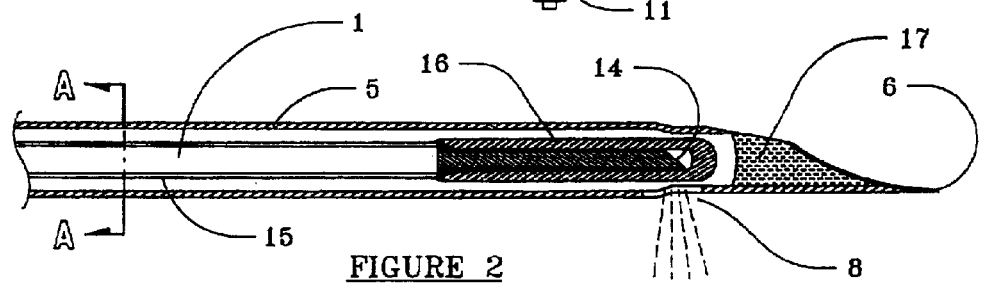
FIG. 2 is an enlarged, partial, cross-sectional, side elevational view of the distal end portion of the optical fiber and the catheter sheath of the device of FIG. 1 terminating in a sharp needle end.
Figure 3:
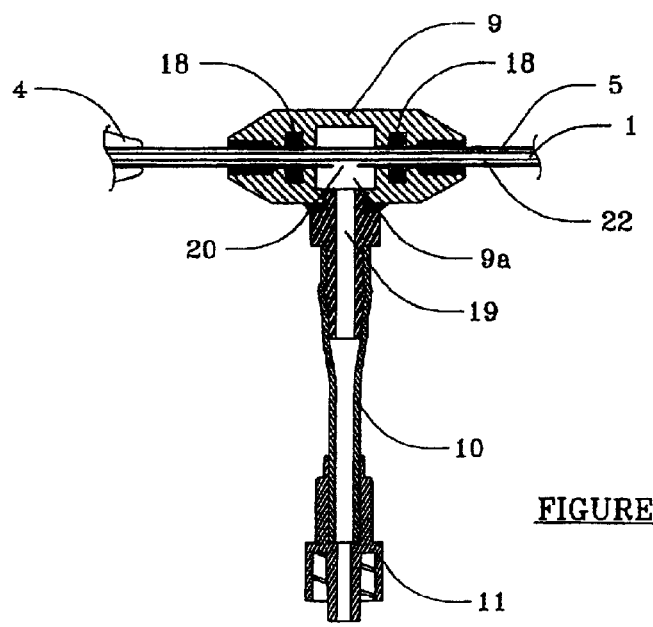
FIG. 3 is an enlarged, partial, cross-sectional, side elevational view of the fitting and fluid/vacuum port of the device of FIG. 1.

FIGS. 1–3 illustrate one embodiment of a catheter device 100 constructed in accordance with the present invention. The device 100 incorporates an elongated quartz or fused silica optical fiber 1 extending from a connector 2 which optically couples the optical fiber 1 to a source of laser energy 3 through an elongate tubular handpiece 4 and a hollow elongate generally cylindrically shaped metal tube 5 which extends distally and co-axially from the handpiece 4. A proximal end of tube 5 extends at least partially through the handpiece 4 and is secured therein. The distal end of tube 5 is closed ended and shaped, for example, into a sharp needle point 6 to facilitate the penetration thereof into the area of the tissue to be vaporized. Handpiece 4 bears a tactile button 7, located on the side of handpiece 4 opposite the direction of laser beam emission, as shown by the arrows, from a laser emission port or aperture 8 formed in the lower peripheral distal end wall portion of tube 5.

Surrounding and mounted to the proximal end of tube 5, adjacent the handpiece 4, is a hollow fixture or fitting 9 which couples the handpiece 4 to tube 5 and, as shown in FIG. 3, defines an interior cavity 9a in fluid or gas flow communication with an inlet port or aperture 20 formed in a lower proximal end wall portion of tube 5. The fitting 9 has a hollow elongate arm or port 10 depending downwardly therefrom and terminating in a luer lock 11 adapted for connection to a source of fluid or vacuum (not shown). Tube 5 also includes a fluid outlet port or aperture 12 (FIG. 1) formed in a lower wall portion thereof and positioned approximately 30 cm proximal of the laser energy emission port or aperture 8 thereon. Fluid outlet port or aperture 12 may be positioned on the same side of the wall of tube 5 as the laser emission port 8 (FIG. 1), or on any other surface of the wall of tube 5. Markings 13 (FIG. 1) on tube 5 indicate, for example, in 1 cm or shorter intervals, the distance from laser emission port 8 along the shaft of tube 5.

As seen in FIG. 2, optical fiber 1 extends generally longitudinally through the handpiece 4, the fitting 9, the interior of tube 5 and terminates in tube 5 at a point opposite and generally aligned vertically with the location of the laser emission port 8 such that the distal end of the fiber 1 is visible through the port 8. The optical fiber 1 is spaced from the interior surface of the wall forming tube 5 and thus is spaced and aligned generally parallel to the ports 8, 12 and 20 formed in tube 5. The distal radial end surface of optical fiber 1 has been ground to a flat 30° to 50° angle beveled surface 14, preferably a surface beveled at an angle of about 40°, which extends angularly inwardly and proximally in the direction of the outlet port 12 (FIG. 1) and facing away from laser emission port 8. The beveled surface 14 allows laser energy emitted from the fiber optic 1 to be directed through the laser emission port 8 at an angle of about 80° to about 90° relative to the longitudinal axis of the fiber optic 1 and tube 5.

Optical fiber 1 includes a top buffer coat and underlying vinyl cladding 15 which have been removed from the distal end portion thereof to define a bared distal fiber end portion. A quartz or fused silica capillary tube 16, whose body is hollow and whose distal end is closed ended, is disposed over and surrounds the bared distal end portion of optical fiber 1, and its proximal end may be affixed to bared optical fiber 1 by thermal fusion or to buffer coat and vinyl cladding 15 thereof by an adhesive. According to the present invention, capillary tube 16 prevents fluid from contacting the beveled distal end surface 14 of optical fiber 1. An air interface or gap between the tube 16 and the beveled surface 14 of optical fiber 1 is necessary for total internal reflection of the light energy, as shown by the arrows. Tube 5, which may be made of medical grade stainless steel such as used in syringe needles may, as described above, have a sharp distal end terminating in the point 6 as shown in FIG. 1, or a beveled distal end surface terminating in a point, as shown in FIG. 2, which is common in syringe needles, to facilitate its entry into the tissue. To prevent tissue and blood from entering the open, beveled distal end of rod 5, the interior of the distal end of rod 5 may be filled with an adhesive or other biologically compatible material 17.

FIG. 3 illustrates the means by which fluid may be infused into the rod 5 to cool the distal end of tube 5 and capillary tube 16 and also to clean any tissue debris from the light emitting quartz or silica surface of capillary tube 16. Fitting 9 which includes a hollow interior or cavity 9a is mounted for rotation about the tube 5, adjacent the distal end of handpiece 4. "O" rings 18 create a seal between the hollow interior 9a and the proximal and distal ends of fitting 9 and tube 5. Fitting 9 has a hollow arm or elongate port 10 in fluid communication with an opening or port 19 in the lower wall of the fitting 9 which, in turn, is in fluid flow communication with the co-axially aligned inlet opening or port 20 in tube 5. The arm 10 terminates in the standard luer lock 11, to which a source of fluid, such as a syringe pump, roller pump, syringe or bag of fluid (not shown) may be attached. A pair of flanges or couplings 21, attached to and surrounding the tube 5, and in turn surrounded by the fitting 9, prevent fitting 9 from moving longitudinally along tube 5. The "O" rings 18 surround the ends of the couplings 21 and contact the interior surface of the wall of the fitting 9.

Port 19 allows fluid to enter the space 9a between the lumen of fitting 9 and the exterior of tube 5, and port 20 allows fluid to enter the space between the lumen of tube 5 and optical fiber 1, regardless of the axial position of fitting 9 on tube 5. Alternatively, suction may be applied through the arm 10 of FIG. 3, utilizing a vacuum pump, a syringe or other means (not shown), as known in the art. All references to fluid infusion herein also apply to the use of a vacuum or suction process.

While the use of a metal hollow tube 5 to enclose the beveled optical fiber/capillary tube assembly is described herein, a plastic tube or hollow rod (not shown) may be substituted for metal tube 5, with a short length of syringe needle attached to its distal end, to facilitate the device's penetration into tissue. The distal end of the syringe needle is plugged with an adhesive as described above.

Figure 4A:
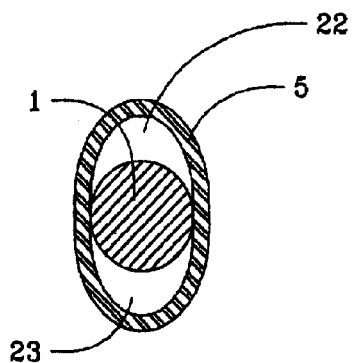
FIG. 4(a) is an enlarged, cross-sectional view taken along plane A—A in FIG. 2 showing the manner in which a portion of the sheath is flattened to the optical fiber to create passageways between the sheath and the optical fiber.

As seen in FIG. 4(a), distal portion of tube 5 has, in one embodiment, been flattened to the outer surface of the optical fiber 1 at the 3 o'clock and 9 o'clock positions. The inner surface of the wall of the tube 5 is forced to contact the outer surface of the fiber 1 and to compress inwardly into an oval or elliptical shape so as to create upper and lower fluid channels or passageways 22 and 23 in the tube 5.

Figure 4B:
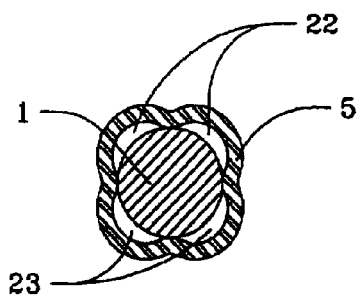
FIG. 4(b) is an enlarged cross-sectioned view illustrating an embodiment where the sheath is crimped to the optical fiber so as to create plural passageways.

FIG. 4(b), which is a cross-section of the device of FIG. 2, taken through plane A—A, illustrates an embodiment where tube 5 is crimped to the outer surface of fiber 1, thereby defining a pair of upper fluid channels 22 and a pair of lower fluid channels 23.

Figure 5:
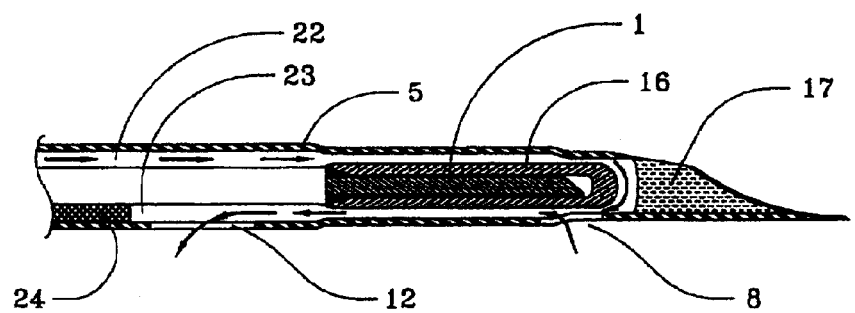
FIG. 5 is an enlarged, partial cross-sectional, side elevational view of the distal end of the device of FIG. 2 depicting the flow of fluid therethrough.

The crimped distal end portion of tube 5 is shown in FIG. 5. Particularly, tube 5 is crimped generally from the proximal end of the capillary tube 16 to the proximal end of tube 5 terminating in handpiece 4. As shown in FIG. 5, channel 22 is in fluid flow communication with the channel 23 and the inlet port 20 in tube 5 while the channel 23 is in fluid flow communication with the outlet port 12 in tube 5. Channel 22 enables fluid to flow over the distal end of capillary tube 16 so as to cool and clean capillary tube 16 as well as metal tube 5, to flow into channel 23 and exit therefrom via outlet port 12 in metal tube 5. Fluid channel 23 is plugged with adhesive 24 proximal to fluid exit port 12 in the tube 5, and fluid exit port 12 has a width or diameter greater than the laser emission port 8 in the tube 5.

Fluid will take the path of least resistance in a generally oval shaped pattern, as shown by the clockwise arrows, and flow through fluid channel 22 in the direction of the distal end of the tube 5, over the top surface of capillary tube 16, to counter any heat build-up on the top (non-laser emitting side) of capillary tube 16 and tube 5, then over and around the distal laser emission surface of capillary tube 16, to cool it and wash away debris, then rearwardly thereof through the lower fluid channel 23, and then out of the tube 5 through the fluid exit port 12. Adhesive plug 24 in the portion of the channel 23 proximal to port 12 (FIG. 5) prevents and blocks the further rearward flow of the fluid through the tube 5. Likewise, the adhesive blocks the flow of fluid through channel 23 upon introduction of the fluid through the inlet port 20. Hot gasses, created by the vaporization of tissue by the laser energy, may also enter laser emission port 8, travel rearwardly through fluid channel 23 and exit tube 5 through fluid exit port 12 which, as described above, is located at a point remote from the tissue being treated.

While a small amount of the infused fluid will be vaporized by the laser energy as it passes over the laser emission surface of capillary tube 16, little, if any, of the infused fluid will exit through laser emission port 8, as the pressure created by hot gasses from the vaporization of tissue will force the fluid and the hot gasses themselves to exit through the channel 23 and out through the fluid exit port 12. If these gasses are not allowed to exit, excessive coagulation of tissue and damage to the distal end of optical fiber 1, capillary tube 16 and tube 5 may result.

Figure 6:
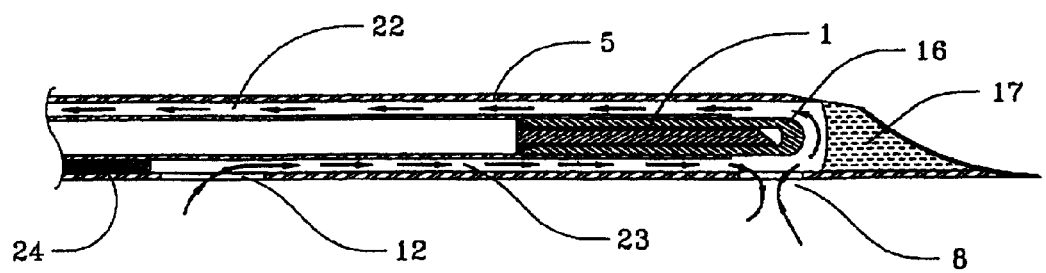
FIG. 6 is an enlarged, partial, cross-sectional, side elevational view of the distal end of the device incorporating the catheter insert of FIGS. 9 and 10 and depicting an alternate fluid flow pattern therethrough.

Alternatively, as shown in FIG. 6, if negative pressure is applied to channel 22, fluid is drawn into channel 23 through the port 12 and then flows in and around the capillary tube 16 in a counter-clockwise direction into channel 22.

Figure 7:
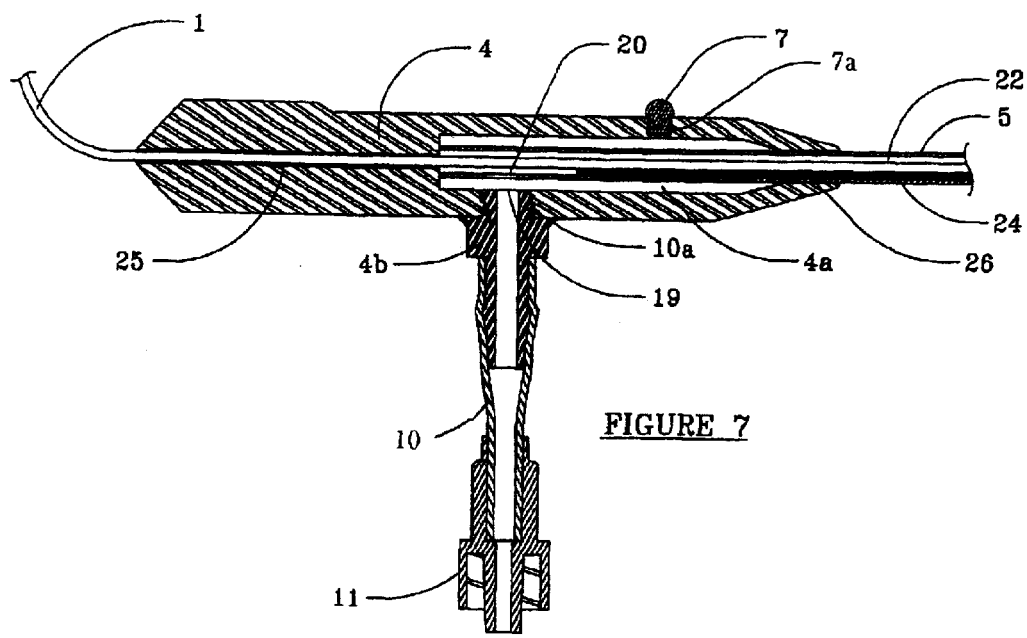
FIG. 7 is an enlarged, partial, cross-sectional, side elevational view of an alternate embodiment of the handpiece and fluid/vacuum coupling port of the device of the present invention.

FIG. 7 illustrates an alternate embodiment of the handpiece 4 of the device of FIG. 1 where the arm 10 is integrally associated with handpiece 4 rather than fitting 9 (FIG. 3). As can be seen, optical fiber 1 is affixed to handpiece 4 by adhesive 25 and extends through the handpiece 4 and then tube 5, whose proximal end portion is affixed to handpiece 4 by adhesive 26 and extends into and through a longitudinal generally cylindrically shaped interior cavity 4a which extends from the distal end of the handpiece 4 into the body thereof. Button 7 may be friction fitted into a recess 7a found in an upper portion of the outer surface of the handpiece 4 or fixed therein by an adhesive. The handpiece 4 includes a lower threaded aperture 4b extending between the cavity 4a and the lower outer surface thereof. The arm 10 incorporates a threaded coupling 10a for threadingly engaging threaded aperture 4b and securing the arm 10 to the handpiece 4. Tube 5 is positioned inside the handpiece 4 such that the aperture 20 of tube 5 is positioned generally co-axially opposite and spaced from the aperture 4b of handpiece 4.

In accordance with this alternate embodiment, fluid may be infused in a manner similar to that described above with respect to FIG. 5, through the female luer lock 11, through arm 10, through port 19 into cavity 4a, through opening 20 in tube 5 and then into fluid channel 22. As described above, fluid cannot enter lower fluid channel 23, as it has been occluded distally between the opening 20 and the exit port 12 with adhesive 24. Alternatively, negative pressure may be applied to luer lock 11 as described above with respect to the FIG. 6 embodiment.

Figure 8:
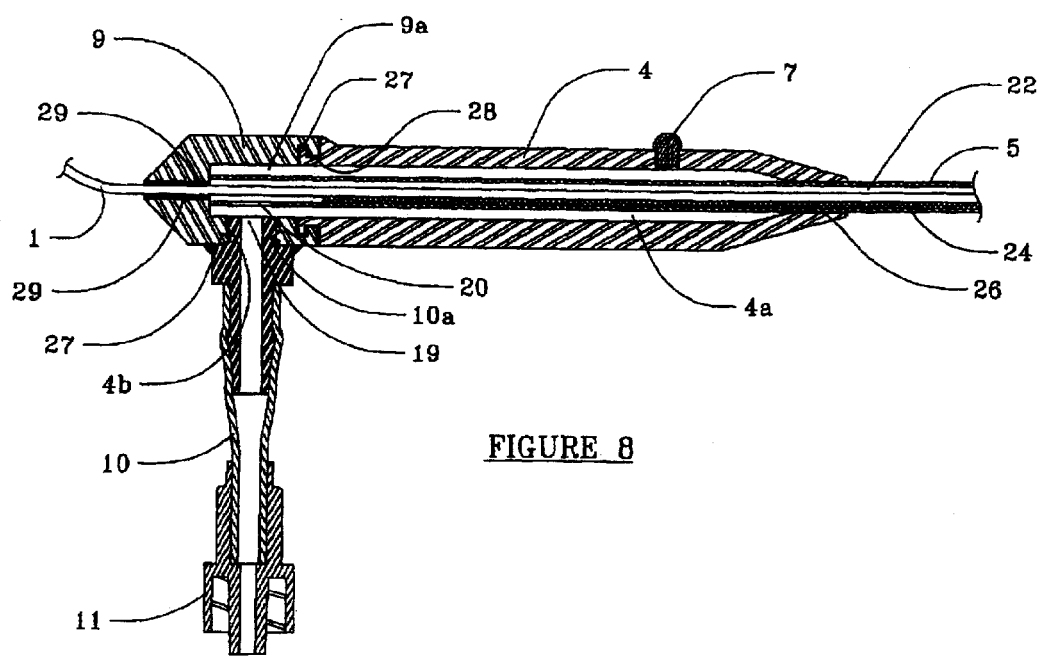
FIG. 8 is an enlarged, partial, cross-sectional, side elevational view of another alternate embodiment of the handpiece and fluid/vacuum port of the device of the present invention.

As seen in FIG. 8, which depicts another embodiment of the handpiece 4 and the fitting 9 of the device of the present invention, fitting 9 is rotatably attached to the proximal end of handpiece 4 as shown. The flange 27 in handpiece 4 extends circumferentially outwardly from the distal end portion of handpiece 4 and defines circumferential recess 28. The end portion of the fitting 9 is fitted into the recess 28 in the handpiece 4 for coupling the handpiece 4 to the fitting 9.

In this embodiment, the fitting 9 includes a longitudinal central cavity 9a in communication with a longitudinal central cavity 4a in the handpiece 4. The tube 5 and optical fiber 1 extend through the respective cavities 4a and 9a.

As described earlier in connection with FIGS. 3 and 7, fluid may be infused through female luer lock 11, arm 10, opening 19 in fitting 9 and opening 20 in tube 5, and into fluid channel 22 (fluid channel 23 having been occluded by adhesive plug 24 in a manner similar to that described above). Tube 5 is affixed to handpiece 4 by adhesive 26. Gasket 29 surrounds the portion of the fiber 1 extending through the proximal end of the fitting 9 and forms a fluid seal to prevent fluid egress from the space between optical fiber 1 and the cavity 9a in fitting 9, while permitting fitting 9 to rotate about optical fiber 1, the proximal end of tube 5 and handpiece 4.

In this embodiment, handpiece 4 and attached tube 5, containing optical fiber 1, can be rotated, without requiring the source of fluid or suction to be likewise rotated, reducing drag in the hand of the operator. Alternatively, suction may be applied to luer lock 11.

Figure 9:
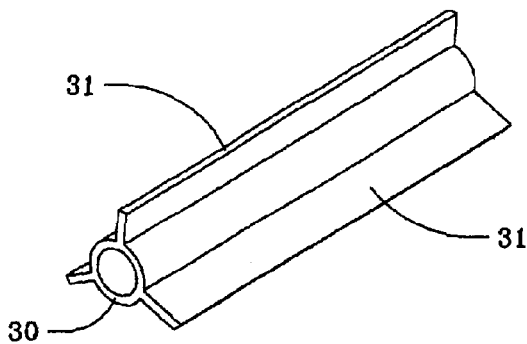
FIG. 9 is a perspective view of a catheter insert for the tube of the device of FIG. 1.

As seen in FIG. 9, the device of the present invention may alternatively incorporate a plastic elongated tubular insert 30, whose inside diameter is only slightly larger than the outside diameter of optical fiber 1, and is extruded with at least two spaced apart longitudinally extending tines, splines, fins or walls 31, preferably three tines 31.

The insert 30 of FIG. 9, for example, may be extruded from materials such as polyvinylchloride (PVC), polyurethane, polypropylene, polyethylene or tetrafluoroethylene, e.g., Teflon®. A fluid such as saline may be infused into fluid inflow channel 22 as described above at a rate of about 1 to 10 cc per minute, preferably about 2 to 6 cc per minute.

Figure 10:
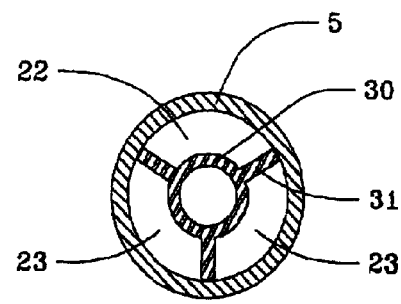
FIG. 10 is an enlarged, cross-sectional, side elevational view taken along the plane B—B in FIG. 11 depicting the tubular catheter insert positioned in the interior of the tube of the device of FIG. 11.
Figure 11:
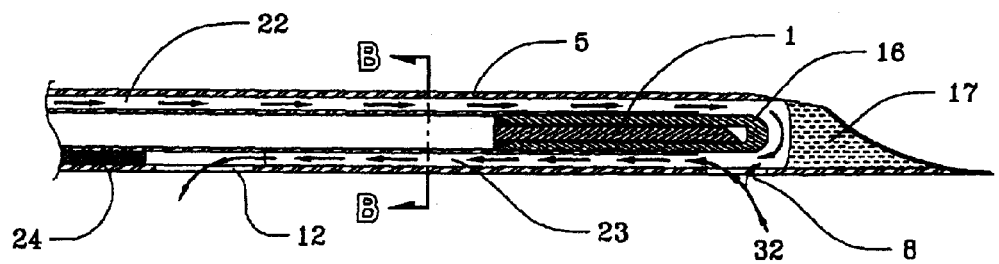
FIG. 11 is an enlarged, partial, cross-sectional, side elevational view of the distal end of the device incorporating the catheter insert of FIGS. 9 and 10 and depicting one selected fluid flow pattern therethrough.

As seen in FIG. 10, which is a cross-sectional view of the device of FIG. 11, taken through plane B—B, the tines or fins 31 extend perpendicularly outwardly from the outer surface of the insert 30 and are spaced around the circumference thereof. In the embodiment shown, the tines 31 are located generally at the 10 o'clock, 2 o'clock and 6 o'clock positions of insert 30. As shown in FIG. 10, the optical fiber 1 extends through the interior of the insert 30. The optical fiber 1-plastic insert 30 assembly is disposed within the lumen or interior of tube 5, with the outer peripheral faces of the tines 31 contacting the inner surface of tube 5, to form the fluid inflow channel or passageway 22 and two fluid outflow channels or passageways 23.

The distal end of insert 30 is positioned generally adjacent the proximal end of capillary tube 16 and aft of the emission port 8. An adhesive or the like 24 is used to close both fluid outflow channels 23 aft of the fluid exit port 12, which adhesive extends rearwardly and terminates just distally of the opening 20 in tube 5, as shown in FIG. 5. The tines 31 are spaced about the outer surface of insert 30 such that the combined area of the lumens of the fluid outflow channels 23 distal to fluid exit port 12 are significantly greater then the area of the lumen of fluid inflow channel 22. Also as seen in FIG. 5, fluid exit port 12 is larger than laser emission port 8, creating a path of least resistance for fluid flow and hot gasses flowing out through the fluid exit port 12.

In a similar manner to that described above with respect to FIGS. 3 and 7, fluid from a source (not shown) passes through fluid channel 22 as shown by the clockwise arrows in FIG. 5 and cools the upper face of the closed distal end portion of capillary tube 16 which encases the distal, beveled end of optical fiber 1 and tube 5, then passes around, cools and flushes debris from the laser emitting distal end surface of capillary tube 16, then through the two fluid channels 23 and then exits the device through fluid exit port 12, outside the area of tissue being treated. As also described above, the fluid cannot proceed further through fluid exit channels 23 due to adhesive 24, which is disposed therein.

As shown in FIG. 11, arrow 32 indicates the direction of flow of hot gasses resulting from the vaporization of tissue through laser emission port 8, into fluid exit channel 23 and then through the exit port 12. The pressure of hot gasses from the vaporization of tissue by laser energy opposes fluid flow through channel 22 and does not permit a substantial amount of the cooling fluid to exit through laser emission port 8. In all of the described embodiments, fluid exit port 12 is preferably located about 3 to 30 cm, preferably about 4 to 10 cm, proximal and aft of the laser emission port 8, a distance sufficient to place the fluid exit port 12 outside of the area of the tissue being treated (i.e., outside the body or in the lumen of a vessel, duct, organ or surgically created passage which is being cooled by fluid infused independently through an endoscope or catheter).

If a negative pressure is applied to channel 22, fluid is drawn into port 12 and hot gases from the vaporization of tissue are drawn through laser emission port 8. Both exit through channel 23 and pass through the handpiece and fitting shown in FIG. 7 into a vacuum collection bottle, syringe or other means, as is known in the art.

Figure 12:
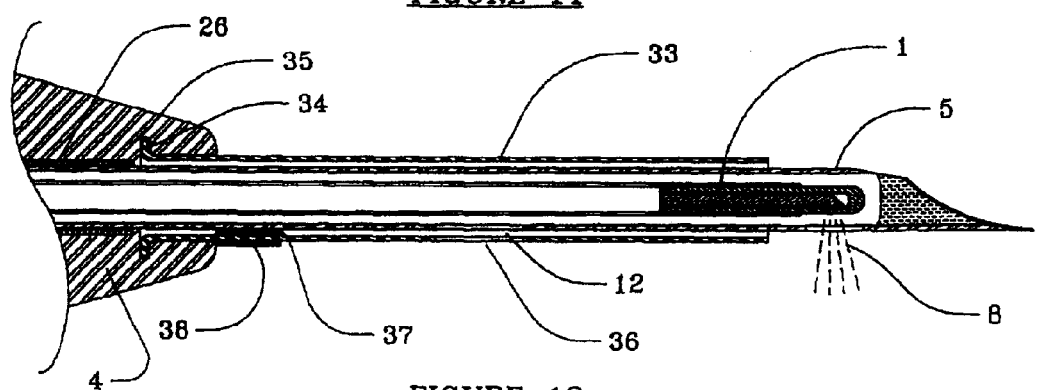
FIG. 12 is an enlarged, partial, cross-sectional, side elevational view of the device of FIG. 1 with a sleeve surrounding the tube.
Figure 13:
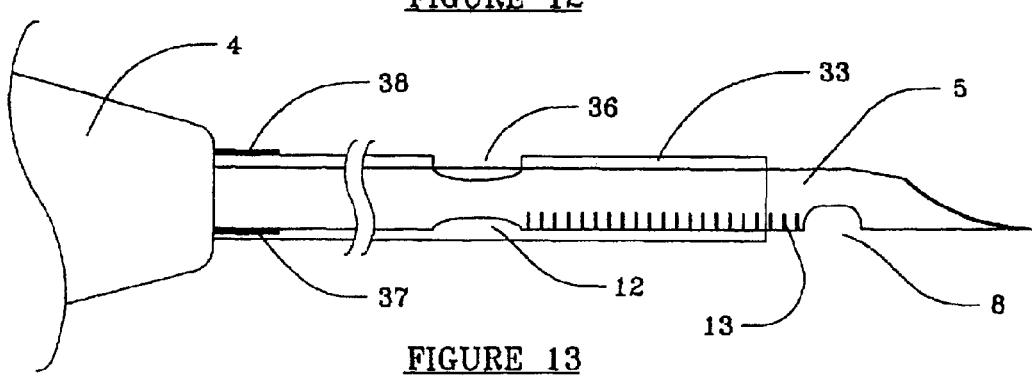
FIG. 13 is an enlarged, partial, side elevational view of the device of FIG. 12.

As seen in FIGS. 12 and 13, a thin plastic sleeve or sheath 33, preferably made of Teflon® or other lubricious, clear plastic material, may be disposed over and surround all but the distal end portion of the tube 5, to reduce friction with and prevent tissue adherence to the tube 5. The distal end of sleeve 33 terminates at a point aft of the laser emission port 8. Also, sleeve 33 insulates the tube 5 and prevents heat, conducted along the tube 5, from coagulating tissue along the puncture channel, causing edema and delaying healing.

While plastic sleeve 33 can be fixedly attached to tube 5, in the embodiment of FIGS. 12 and 13, plastic sleeve 33 is rotatable about tube 5 and the handpiece 4. The proximal end of plastic sleeve 33 has been formed and bent upwardly to form a circumferentially extending flange 34, which is disposed and fitted within a circumferential recess 35 extending inwardly into the body of the handpiece 4 from the inner surface of the handpiece 4 defining the cavity 4a therein. The flange/recess combination allows the sleeve 33 to be rotated relative to the handpiece 4 and the tube 5. As shown, a port 36 formed in the wall of the plastic sleeve 33 is aligned with fluid exit port 12 of tube 5. In the position of FIG. 12, markings 37 and 38 located at the proximal end outer surfaces of the rod 5 and plastic sleeve 33 respectively, are aligned so as to align the sleeve port 36 with port 12 of tube 5.

As seen in FIG. 13, an external, side view of the device of FIG. 12, markings 13 on tube 5, proximal to laser emission port 8, can be seen through plastic sleeve 33, enabling an operator to visually (through an endoscope) ascertain the depth to which tube 5 has been inserted into tissue. As shown, sleeve 33 has been rotated 180° over the tube 5, so that fluid exit port 12 is covered by the sleeve 33. In this position, marking 37 on tube 5 and marking 38 on sleeve 33 are no longer aligned and are located on opposite sides of the tube 5. The ability to open or close exit port 12 on tube 5 by rotating sleeve 33 enables fluid to be infused through fluid inflow channel 22 during all or the first portion of the lasing procedure and, after rotating the plastic sleeve 33 by 90° or more, preferably 180°, permits a vacuum to be drawn during all or the second portion of the lasing procedure and, if desired, afterwards, to collapse the tissue whose inner portion has been vaporized.

Alternatively, a vacuum can be drawn through channel 22 during all or the first portion of the lasing procedure to evacuate the hot gasses created by vaporization of tissue and, after rotation of sleeve 33, fluid to cool the distal end of the device can be infused during all or the second portion of the laser procedure through channel 22 and, if desired, afterwards to cool the tissue.

Figure 14:
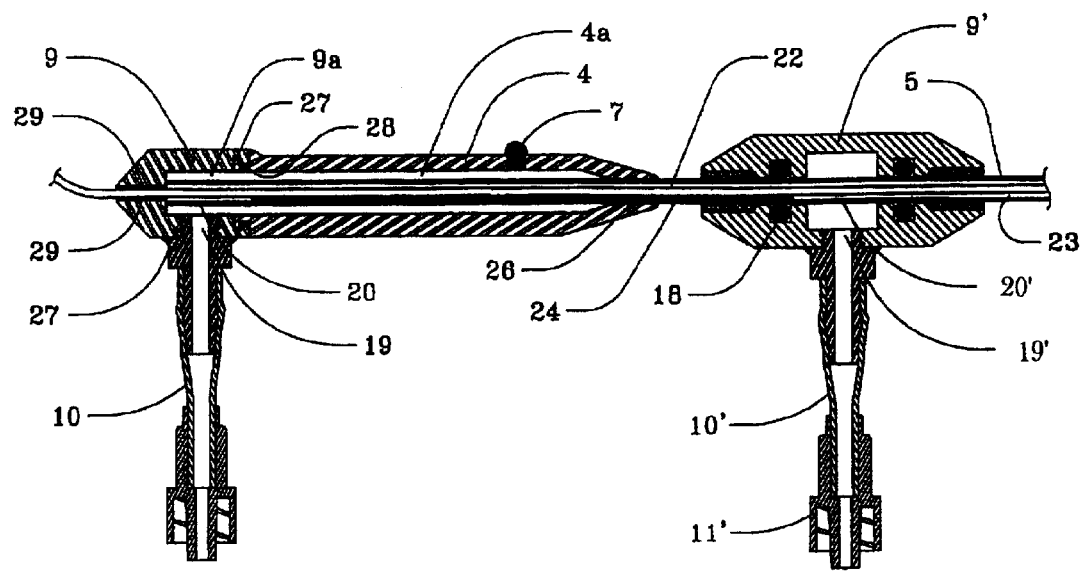
FIG. 14 is a enlarged, reduced partial, cross-sectional, side elevational view of the entire device of FIG. 7, with ports for simultaneous infusion of fluid and drawing of a vacuum operably associated with the handpiece and the fitting, respectively.

As seen in FIG. 14, the device of FIG. 1 may alternatively be configured such that fluid may be infused through the luer lock 11 of a first arm 10, and suction may be simultaneously applied through a luer lock 11' of a second arm 10'. In this embodiment, the arm 10 with luer lock 11 is operably and threadingly associated with the handpiece 4 in the manner as described above with respect to FIG. 8. The second arm 10' with luer lock 11' is operably associated with a fitting 9' in the manner described with respect to FIG. 3 above and is mounted fore of the handpiece 4. Particularly, tube 5 and optical fiber 1 extend first through the cavity 9a defined in the fitting 9 and then through the cavity 4a defined in the handpiece 4 to define a device incorporating two spaced apart arms 10 and 10'. The tube 5 incorporates a first proximal port 20 in fluid flow communication with the first arm 10 including luer lock 11 and a second distal port 20' in fluid flow communication with the second arm 10' including luer lock 11'.

In this embodiment, the portion of the outflow channel 23 extending between the proximal port 20 and the distal port 20' has been blocked out or filled with an adhesive 24. In this embodiment, there is no fluid exit port in tube 5, and fluid is infused in a clockwise direction through the arm 10 with luer lock 11, then through the various ports and cavities as described above with respect to the other embodiments through the channel 22 and into and around the distal end portion of the capillary tube 16 as also described above to cool the tip. The fluid and hot gasses from the vaporization of tissue are then drawn into the channel 23 by a vacuum which can be applied through luer lock 11' and may be deposited in a vacuum collection bottle, a syringe or other device operably associated with the luer lock 11' (not shown), by means known in the art.

In this embodiment, vacuum plus the pressure of gasses formed by the vaporization combine to effect faster and more efficient removal of fluid and hot gasses from the tissue opposite laser emission port 8.

Figure 15:
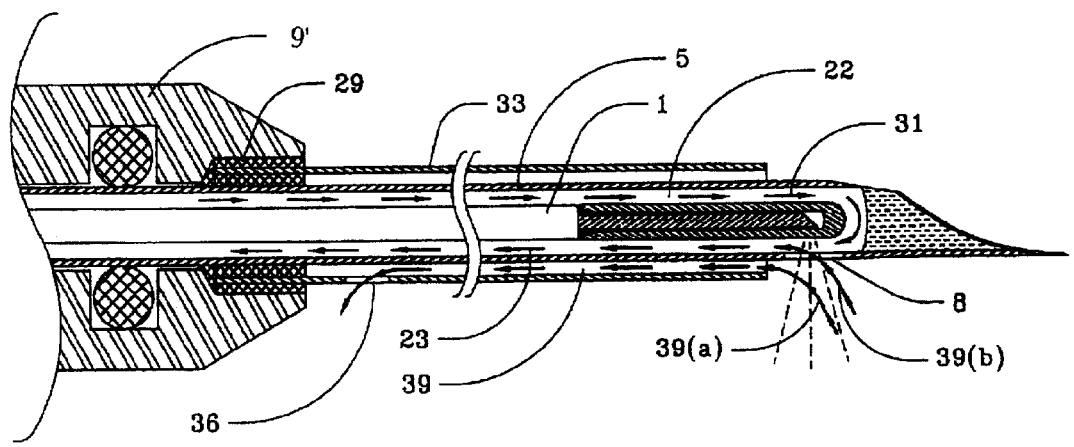
FIG. 15 is an enlarged, partial, non-sectional view of device embodying the present invention similar to FIG. 14 and provided with a plastic sheath that extends from the distal end of the handpiece.

An alternate, preferred embodiment of the present invention is shown in FIG. 15. In this embodiment, the proximal end of plastic sheath 33 is fixedly attached within the distal end of the fitting 9' of FIG. 14 by adhesive 29. Sheath 33 has at least one port 36 near its proximal end, outside the body. Hot gasses from the vaporization of tissue enter the space 39 between sheath 33 and hollow metal tube 5, as shown by arrow 39(a), and exit through port 36 in sheath 33 into the atmosphere.

As also seen in FIG. 15, fluid can flow through channel 22, as shown by arrows 31. Negative pressure is applied to channel 23, and fluid from channel 22 and hot gasses from the vaporization of tissue are drawn into port 8 in metal tube 5, as shown by arrow 39(b), and pass through channel 23, as described heretofore.

A more preferred embodiment of the device of the present invention is shown in FIG. 16, in which fitting 9, as shown in FIG. 14, is used to infuse fluid through channel 22, created by the space between optical fiber 1 and the interior surface of metal tube 5. However, in this embodiment, adhesive plug 24 shown in FIG. 14 is eliminated.

Fitting 9' is rotatably disposed on metal tube 5. "O" ring 18 creates a fluid tight seal between fitting 9' and metal tube 5. The proximal end of plastic sleeve or sheath 33 is fixedly attached within the distal end of fitting 9' by adhesive 26. Sheath 33, in this embodiment, has no ports in its proximal end.

In use, fluid is infused through fitting 9 into channel 22, about optical fiber 1, at a rate of 1 to 10 ml per minute, preferably about 2 to 6 ml per minute. Vacuum may be applied through fitting 9' to draw hot gasses from the vaporization of tissue and any fluid not vaporized by the laser energy into the space between tube 5 and the interior of sheath 33.

This embodiment is simpler to manufacture and more efficiently removes excess fluid and hot gasses from the vaporization of tissue from the target area.

Instead of beveling the distal end of the optical fiber 1 at an angle of about 30° to 50°, preferably about 39° to about 40°, and encasing it in capillary tube 16 to obtain total internal reflection, as shown in FIG. 17, a reflector composed of gold, silver, copper or other highly reflective material 40 is disposed within the distal end of metal tube 5, whose distal end has been formed into a sharp point 6, or into a beveled syringe shape as shown in FIG. 2. The beveled surface 41 of reflective material 40 is located opposite and spaced from the distal end of optical fiber 1 and generally above the tube emission port 8 and is inclined at an angle of approximately 35° to 55°, preferably at an angle of about 45°, opposite the end face of optical fiber 1, to direct the laser energy through the laser emission port 8 at an angle of about 90° relative to the longitudinal axis of the fiber optic 1 and the tube 5 as shown by the dotted lines. Such devices are more fully described in co-owned U.S. Pat. Nos. 5,242,437, 5,380,317 and 5,649,924, which are fully incorporated herein by reference. Silver is a preferred reflective material, as it is about as efficient a reflector of holmium laser energy as gold or copper, but is significantly less costly than gold and more durable than copper.

Tube 5, has been crimped to optical fiber 1, as described in FIG. 4(a), creating channel 22 and channel 23. A fluid, such as saline or distilled water, may be infused through channel 22 in a similar manner as described above with respect to FIGS. 3 and 5 in a clockwise direction around the distal end of the fiber optic 1 at a rate of about 1 to 10 cc per minute, preferably about 2 to 4 cc per minute, to wash any debris from the surface 41 of reflective material 40 and the tip of the optical fiber 1. Channels 23 enables hot gasses and steam from the vaporization of tissue and cooling fluid to escape through the exit port 12 of tube 5.

Alternatively, a vacuum may be drawn through channel 23 in the same manner as described above with respect to FIG. 6 to remove steam and hot gasses and prevent excessive coagulation of the target tissue and coagulation of tissue along the puncture channel. Although not described in detail below, it is understood that the device of FIG. 17 may be constructed to incorporate any of the previously described handpiece or fitting or sheath embodiments.

In bench testing, devices with a gold, silver or copper reflective material 40 exhibited a transmission efficiency of approximately 95% compared to a transmission efficiency of approximately 90% for devices with an optical fiber whose distal end is beveled at an angle of about 39° to about 40° and encased in a capillary tube, as described above.

FIG. 18 is a cross-sectional view of the device of FIG. 19, taken through plane C—C of FIG. 19. As seen in FIGS. 18 and 19, the insert 30 of the device of the present invention may be substituted with an insert 42 which is extruded of a solid plastic material such as described with respect to the tube 30 and includes a central channel or bore 43 (FIG. 18), just slightly larger in diameter than the diameter of the optical fiber 1 which extends therethrough. The insert 42 additionally includes a separate top arcuate channel or passageway 22 which is formed in the material of the catheter 42 and is spaced from and partially surrounds the channel 43. The catheter 42 also includes a bottom arcuate channel or passageway 23 which is also formed in the material of the catheter 42 and also is spaced from and partially surrounds the channel 43. The channel 23 is larger in volume than the channel 22 and the channels 22, 23 and 43 extend the length of the insert 42.

Channel 22 is in fluid flow communication with a source of fluid and channel 23 may be used for fluid outflow as shown by the clockwise arrows or may be in communication with a vacuum or suction source (not shown) both in the same manner as described above. Particularly, fluid flows into channel 22, as indicated by the clockwise arrows, and flows over and around the distal end and emission surface of capillary tube 16 and into lower channel or channels 23. Likewise, the arrows show the direction of flow of hot gasses from the vaporization of tissue into port 8, through channel or channels 23, and then into a collection means (not shown), as described heretofore. Plastic insert 42 may also be extruded with additional channels for these or other purposes.

As shown in FIG. 19, tube 5 can also include a tip or distal end portion 5a which is secured to a body portion 5b thereof by an overlapping tongue and groove or the like structure 44 associated with the distal end of the body portion 5b and the proximal end of the distal end portion 5a.

Figure 20:
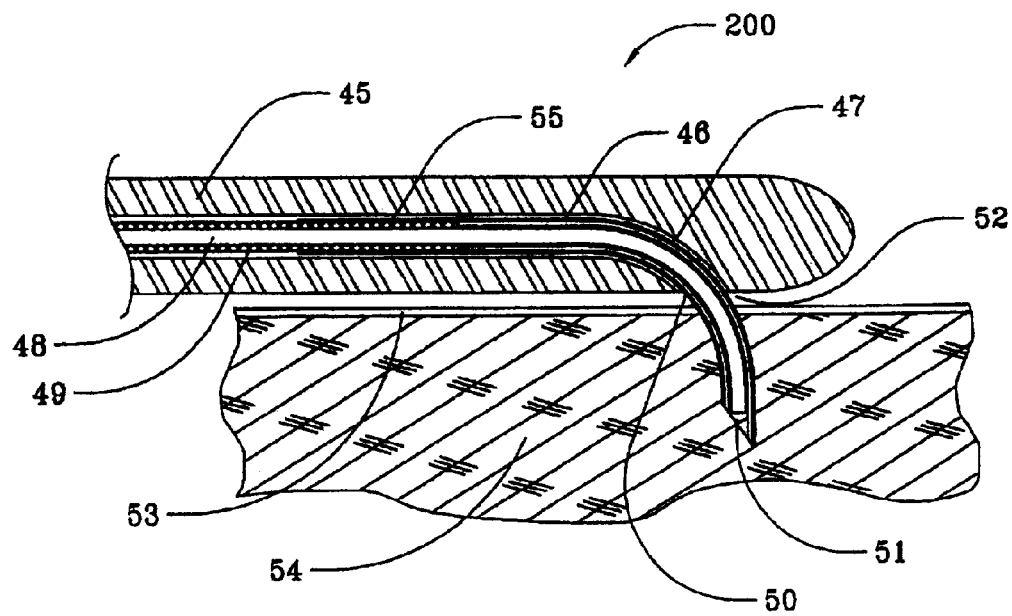
FIG. 20 is an enlarged, partial, cross-sectional side elevational view of yet another embodiment of the device of the present invention.

FIG. 20 illustrates an alternate embodiment of the present invention. Instead of a prism-like refractive means or a gold, silver, copper or other metallic reflector means to deflect the laser energy laterally into the tissue away from the endothelial or urethral surface, this embodiment employs a means to deflect the distal end of the device at an angle of up to 90° or more into the target tissue in a very small space.

As seen in FIG. 20, the device 200 incorporates a plastic or metal rod 45 having a central, longitudinally extending channel 46 whose diameter is larger than the outside diameter of optical fiber 48, which is slidably disposed therein. Channel 46 transitions into a curved or arcuate channel 47, which curves toward and terminates outward in an opening 52 formed in the wall of the rod 45, at a point proximal to the distal closed arcuate end thereof.

In this embodiment, the buffer coating 49 of optical fiber 48 terminates about 2 to 10 cm from the distal end of optical fiber 48, preferably about 3 to 6 cm from its distal end, having been removed therefrom by means known in the art, leaving the glass cladding (not shown) about optical fiber 48 intact.

A hollow cylinder 50 preferably made of a shape memory alloy such as, for example, a superelastic nitinol, such as manufactured by Memry, Inc. of Menlo Park, Calif., which has been heat treated in a bent configuration at an angle up to 90° or more, preferably at least about 30° to 80°, is attached, by crimping or an adhesive, as known in the art, to the bared distal end portion of optical fiber 48. The distal end of hollow cylinder 50 may be beveled into a sharp, syringe needle configuration 51. The distal end face of optical fiber 48 is preferably positioned within the opening 51 of cylinder 50.

While hollow cylinder 50 is confined within channel 46 of rod 45, the cylinder 50 is constrained from its heat treated, curved shape. When the distal end portion of hollow cylinder 50, containing bared optical fiber 48, is manually advanced into curved channel 47 and out through the opening 52 in rod 45, by means located outside the body (not shown), cylinder 50 returns to its heat treated, curved shape, penetrates endothelial surface 53 and enters tissue 54 at a combined angle of up to 90° or more.

Fluid may be infused or a suction may be drawn through the space between the exterior surface of optical fiber 48 and the interior surface of hollow cylinder 50, or the space between the exterior of cylinder 50 and the interior surfaces of channels 46 and 47. Optionally, a hollow sleeve 55 composed of a plastic, such as Teflon®, may extend over the exterior of hollow cylinder 50. Sleeve 55 prevents tissue from sticking to the exterior of hollow cylinder 50, insulates the tissue from heat conducted along cylinder 50, and enables gasses from the vaporization of tissue to escape through the space between the exterior surface of hollow rod 50 and the interior surface of sleeve 55, as well as between the tissue and the nonstick exterior of sleeve 55.

Such a device may be used to emit laser energy into the prostate gland without damaging the male urethra and its underlying supporting tissue, as well as the esophagus in the region of the sphincter, or the female urethra beneath the bladder, without damaging their sensitive endothelial lining.

If RF energy is emitted through metal electrodes inserted into tissue, the metal electrodes become very hot, conduct heat along their length and can damage the delicate endothelial surface of the tissue into which they were inserted, for example, the urethral surface of the prostate, the endothelial surface of the esophagus in the area of the sphincter or the endothelial surface of the female urethra below the bladder. Fluid channels are needed to cool the endothelial surface and temperature sensors at the endothelial surface are needed to sense the temperature and halt the RF procedure if the damage threshold is reached. In addition to failing to complete the procedure, an expensive temperature monitoring, display and control system is required, which also increases the risk of an electrical or computer malfunction.

Figure 21:
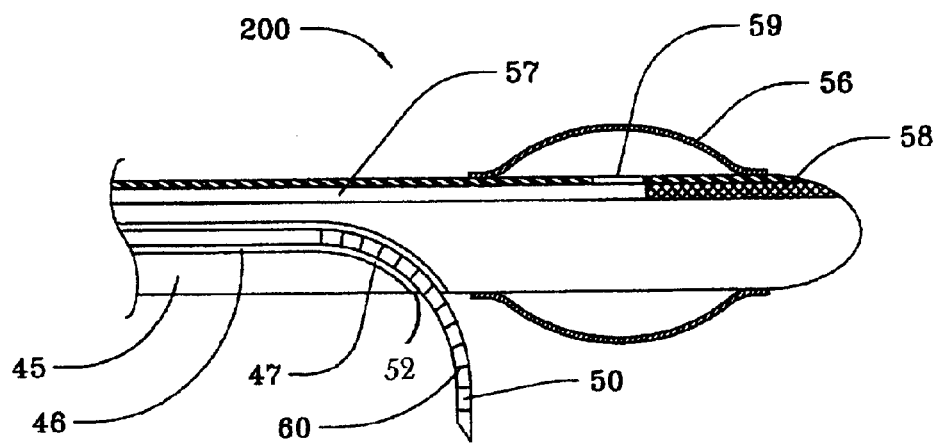
FIG. 21 is an enlarged, partial, cross-sectional, side elevational view of the distal end of the device of FIG. 20 with an inflatable balloon surrounding the distal end.

As seen in FIG. 21, a balloon 56, which may be made of a material such as latex, silicone, polyethylene or polyurethane, surrounds the distal end portion of rod 45, distal and fore of the point at which hollow cylinder 50, containing optical fiber 48 (not shown), exits the opening 52 in rod 45. Fluid may be infused as known in the art through an elongate fluid channel 57 formed in and extending through the body of the rod 45 to inflate balloon 56. An opening 59 extending between the channel 57 and the side wall of tube 45 allows for fluid communication between the channel 57 and balloon 56. The portion of the channel 57 located fore of the opening 59 is filled with an adhesive 58 to prevent the flow of fluid therethrough. Balloon 56 may be inflated with a liquid such as saline, a radio opaque or ultrasound opaque fluid or a gas, such as air, $CO_2$, nitrogen or the like.

Balloon 56 centers and stabilizes rod 45 within the duct, hollow organ, cavity or passageway into which the rod 45 is inserted. If the device is used through the working channel of an endoscope, the location of the balloon 56 fore of the rod opening 52 of rod 45 allows a physician to see hollow cylinder 50 as it exits opening 52 and enters the tissue. Markings 60 located on the exterior of cylinder 50 enable the physician to observe how far cylinder 50 has been inserted into the described tissue.

While one optical fiber 48, one hollow cylinder 50, one channel 46 and one curved channel 47 are shown in the rod 45 of FIGS. 20 and 21, more than one of each of the above can be employed in rod 45. Also, curved channel 47 can be eliminated, with optical fiber 48 encased in nitinol cylinder 50 exiting channel 46 directly out of the distal end of rod 45. For example, to shrink or cause scarring in the tissue surrounding the esophagus in the area of the sphincter, two, three, four or more optical fibers 48 may each have their distal ends encased in superelastic hollow nitinol cylinders 50 and each may be manually advanced, together or separately, through channels 46 and 47 and into the target tissue at an angle of up to 90° or more from the axis of rod 45. In this application, rod 45 can have a diameter of about 2 to 16 mm, preferably about 3 to 12 mm. For use in the male urethra to vaporize tissue in the prostate, rod 45, containing one optical fiber 48 and cylinder 50 attached thereto, can have a diameter of about 1.5 to 4 mm, preferably about 2 to 3 mm. For use in the female urethra below the bladder to treat female stress incontinence, rod 45, containing one optical fiber 48 and one cylinder 50 attached thereto, can have a diameter of about 1 to 3 mm, preferably about 1.5 to 2.5 mm.

In an alternative embodiment, cylinder 50 may be eliminated and the diatal end of optical fiber 1 may be beveled into a sharp point, to enable it to more easily penetrate tissue. Optical fiber 1 exits curved channel 47 at an angle in the range of about 20° to about 70° from the axis of rod 45. Optical fiber 1 can contain markings 60 to enable an operator to ascertain the depth to which fiber 1 has been inserted into tissue. Since optical fibers are not thermal conductors, fluid need not be infused to cool the endothelial surface of the tissue into which the optical fiber 1 has been inserted during lasing.

Figure 22:
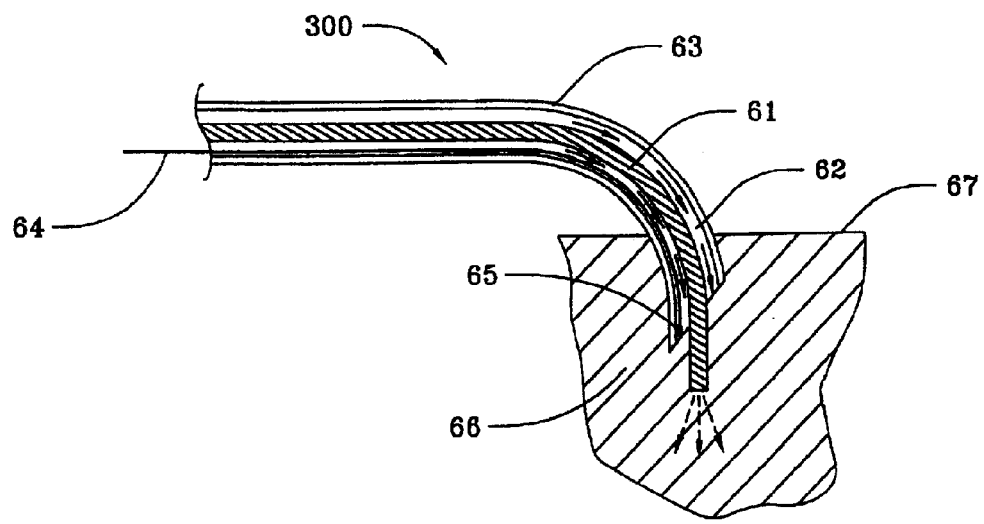
FIG. 22 is an enlarged, partial, cross-sectional, side elevational view of yet a further embodiment of the device of the present invention and depicting one flow pattern of a fluid therethrough.

Yet another device embodiment 300 of the present invention is shown in FIG. 22, in which an optical fiber 61 is slidingly disposed within central channel 62 formed in plastic cannula 63, the distal end of which is beveled, like a syringe needle, to enable it to more easily penetrate tissue. A wire 64, made preferably of nitinol, extends through central channel 62 of cannula 63 and is affixed, as by adhesive or the like, to the distal end of cannula 63 at joint 65 on the inner surface that defines channel 62.

The proximal end of wire 64 is attached to a retractable lever or spool within a handpiece (not shown), as known in the art. When the lever is retracted or the spool is turned, retracting or winding up wire 64, the distal end portion of plastic sheath 63 may be bent or articulated, up to about 90°, as shown.

When cannula 63 is inserted into tissue 66, laser energy can be emitted through optical fiber 61, or optical fiber 61 can be manually advanced out of cannula 61 a desired distance. Preferably, optical fiber 61 is advanced about 2 to about 8 mm into tissue 66, and laser energy can be emitted forwardly, as shown by the arrows.

Optionally, a fluid, such as saline, may be infused into central channel 62, as described above. The fluid flows, as shown by the arrows, through the space between optical fiber 61 and the inner surface of central channel 62 and cools sensitive endothelial layer 67 of tissue 66.

Figure 23:
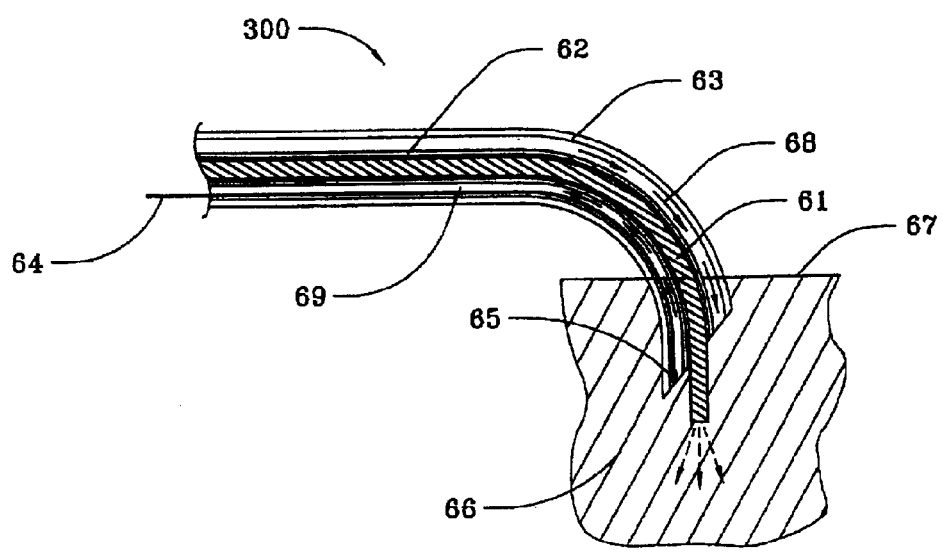
FIG. 23 is an enlarged, partial, cross-sectional, side elevational view of an alternate embodiment of the device of FIG. 20 incorporating a catheter insert and depicting an alternate flow pattern of a fluid therethrough.

As shown in FIG. 23, optical fiber 61 extends through the central channel 62 of a plastic cannula 63, the distal end of which has been beveled, like a syringe needle, and which also contains channels 68 and 69 similar in structure to the channels 22 and 23, respectively, described in FIG. 14, above. In this embodiment, a fluid, such as saline may be infused through the smaller channel 68 to cool the endothelial tissue surface 67, and a vacuum or suction may be applied to the larger channel 69 to remove hot gasses from the vaporization of tissue, in the same manner as described above.

According to this embodiment, wire 64 extends from a retracting mechanism in a handpiece (not shown) through the larger channel 69 and is affixed to the distal end of plastic cannula 63 at point 65 on the inner surface of cannula 63. When wire 64 is extended, the distal end of plastic cannula 63 is bent or articulated as shown in FIG. 23, enabling cannula 63, containing optical fiber 61 to enter tissue 66 at an angle approximately perpendicular to endothelial surface 67 of tissue 66, as described above. Optical fiber 61, optionally, can be advanced out of cannula 63 a desired distance, up to 10 millimeters, into tissue 66, preferably 2 to 8 millimeters When laser energy is emitted through the distal end of optical fiber 61, into tissue 66 as shown by the arrows, a substantial amount of tissue may be vaporized or coagulated while the tissue underlying the endothelial surface 67 is not thermally damaged and the blood supply to the tissue underlying endothelial surface 67 is preserved.

Figure 24:
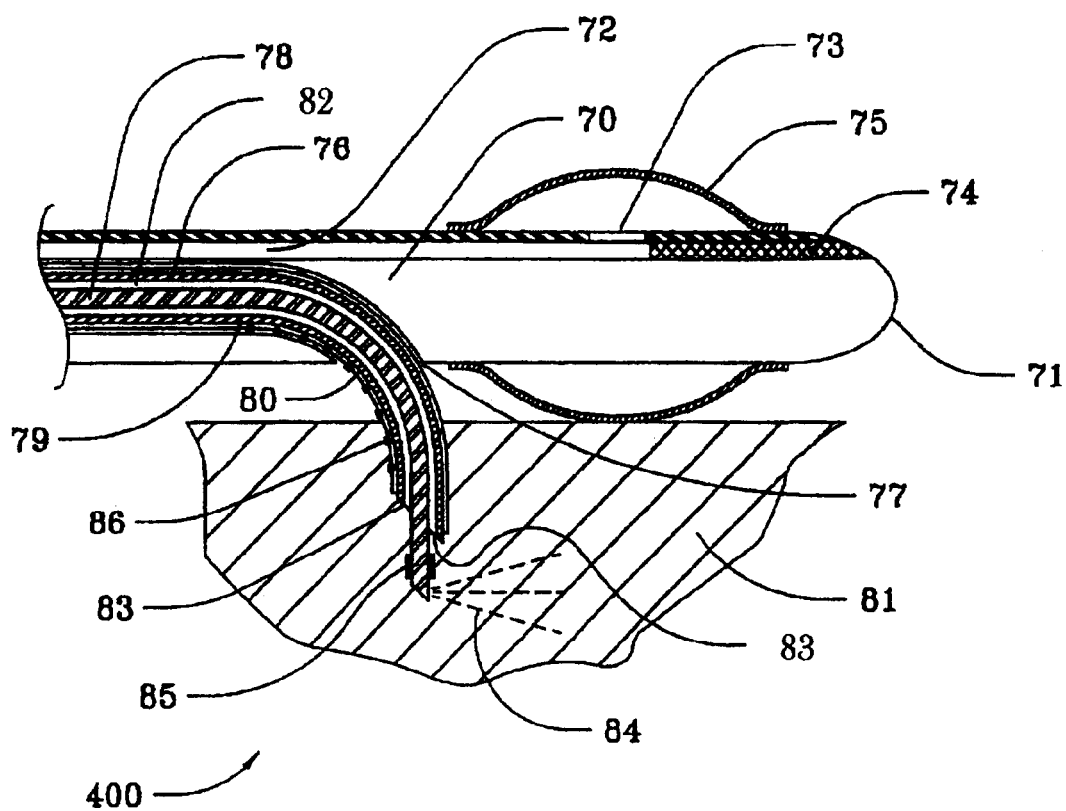
FIG. 24 is an enlarged, partial, cross-sectional side elevational view of yet another embodiment of the present invention.

An alternate embodiment of the device of FIG. 21 is shown in FIG. 24. In this particular embodiment, device 400 includes metal or plastic rod 70, whose distal end 71 is blunt or round ended and which contains inflation channel 72, which is in fluid communication with port 73. The portion of channel 72 distal to port 73 is filled with an adhesive of epoxy 74. The distal end portion of rod 70, including port 73 defined therein, is encased within balloon 75. When fluid is infused through channel 72, balloon 75 is inflated to center and stabilize rod 70 within a duct, blood vessel, body cavity or surgically created passageway. Rod 70 also contains channel 76, whose distal end portion is curved, preferably at an angle of 10° to 50° and exits rod 70 at opening or port 77 in rod 70.

Optical fiber 78, which is disposed within metal sheath 79 having a sharp distal end 83, which is like a syringe needle. Metal sheath 79 may be made of medical grade stainless steel, but, is preferably made of a shape-memory, nickel titanium alloy, whose distal end portion has been heat treated into a curved shape, preferably at an angle of about 20° to about 90°.

Metal sheath 79 is encased within a thin plastic sleeve 80 which is preferably made of a lubricious material such as a fluorocarbon, e.g., a Teflon® material sleeve 80 enables sheath 79 to more easily penetrate tissue, insulates and prevents heat conduction into tissue and prevents tissue from sticking to metal sheath 79.

Optical fiber 78, disposed within sheath 79, is moveably disposed within channel 76 of rod 70. When disposed within channel 76, metal sheath 79 is straight, as the stiffness of rod 70 exceeds the strength of sheath's curvature. When optical fiber 78, sheath 79 and sleeve 80 exit opening 77 of rod 70, sheath 79 is no longer constrained by rod 70 and returns to its heat treated, curved shape, causing optical fiber 78 to assume the same curvature. The combination of the curved distal end of channel 76 and the pre-formed curved shape of sheath 79 results in optical fiber 78, sheath 79 and sleeve 80 entering tissue 81 at an angle of about 60° to about 110°, preferably about 70° to 90°. A vacuum may be drawn through space 82 between optical fiber 78 and sheath 79 by connecting the proximal end of sheath 79 (not shown) to a vacuum or suction source (not shown), utilizing a fitting such as fitting 9 of FIG. 3 or handpiece 24 of FIG. 16 (not shown).

When a vacuum is drawn through space 82 and laser energy is emitted through optical fiber 78, hot gasses from the vaporization of tissue are drawn into space 82, away from the target area within tissue 81, into a collection bottle or other disposal means (not shown). This minimizes coagulation in the target area within tissue 81 and reduces subsequent edema.

While optical fiber 78 may be fixedly attached within metal sheath 79 and may have a flat distal end, so as to emit laser energy forwardly, in the embodiment shown in FIG. 24, optical fiber 78 is moveably disposed within metal sheath 79 and is shown extended distally therefrom. Also, optionally, the distal end of optical fiber 78 may be beveled at an angle of about 30 to 50°, preferably about 39° to about 40°. When laser energy is emitted from optical fiber 78 in a gas environment, which occurs after a few seconds of lasing, energy is emitted from optical fiber 78 by total internal reflection at an angle of about 70° to about 90° from the axes of optical fiber 78, as shown by dotted lines 84. In addition, optical fiber 78 may be rotated to create a larger vaporization zone in tissue 81.

Optionally, a metal or plastic band 85 may be attached to the distal end of optical fiber 78, whose diameter is slightly smaller than the inner diameter of metal sheath 79. Band 85, when the distal end of optical fiber 78 is positioned within the distal end of metal sheath 79, prevents tissue from entering and clogging space 82 between optical fiber 78 and the interior of metal sheath 79, when metal sheath 79 and optical fiber 78 are being inserted into tissue 81.

Markings 86 on plastic sleeve 80 (or alternatively on metal sheath 79, which are visible through plastic sleeve 80) enable the operator to ascertain the depth to which sheath 79, containing optical fiber 78, has been inserted into tissue 81.

Alternatively, the distal end of sheath 79 may be similarly articulated or bent by a wire attached to the distal end of sheath 79 and retracted by a ratchet or worm gear mechanism (not shown), as known in the art.

Lasers which may be used with the device include argon, KTP, Nd:YAG, diode and others. However, these lasers, if fired at 60 watts for 30 seconds at each of 2, 4, 6 and 8 o'clock, create a large coagulation zone (up to 1.5 cm in depth) and little vaporization. Excimer lasers are efficient vaporizers, but are expensive and of limited power. Pulsed Alexandrite lasers, emitting at about 755 nm, modified Nd:YAG lasers emitting at about 1440 nm and holmium:YAG lasers emitting at about 2100 nm, are preferred for vaporization of tissue, with holmium:YAG being most preferred. If holmium:YAG laser energy is to be employed, the optical fiber should be made of quartz or fused silica with a low hydroxyl (—OH) content. If an excimer laser is to be used, the optical fiber should be made of quartz or fused silica with a high hydroxyl (—OH) content. Optical fibers which can be used in the device of the present invention can have a core diameter of about 200 to 1,000 microns, preferably about 300 to 600 microns.

For use in the prostate, the devices of FIGS. 1–19 or FIG. 24 may be inserted into a lobe of an average sized (30 to 40 gram) prostate, with its distal end always at least 0.5 cm beneath the surface, and oriented to fire away from the urethra. For example, a holmium:YAG laser generating 60 watts of power (3 joules per pulse at a repetition rate of 20 pulses per second) for five to sixty seconds, preferably about ten to forty seconds, may be used with constant (saline) flow of about 2 to 6 cc per minute, while rotating the tip of the device through a 90° arc at one or more points about 1 cm apart within the lobes of the prostate (from the veru montaneum to the bladder neck). The device may be rotated through a 90° arc at a rate, for example, of about 90° per second, or advanced and withdrawn while lasing within the lobe at a rate of about 1 cm per second. The metal tube may be first inserted, for example, in the left lobe of the prostate at 2 o'clock and the above described lasing procedures performed. The metal tube insertion and lasing procedures would then be repeated at 4 o'clock in the same lobe, at 8 and 10 o'clock in the right lobe and, if desired, at 6 or 5 and 7 o'clock in the median lobe, if it is significantly enlarged. The method of use of such devices is described in co-owned U.S. Pat. No. 5,437,660, incorporated herein by reference.

At 3 joules per pulse and 20 pulses per second (60 watts) for fifteen seconds, with a device such as shown in FIG. 15, with a plastic sleeve 33, fluid flow and rotation as described above, a Holmium laser will produce a vaporization zone in tissue of about one cm in diameter in each lasing position. If there are a total of 12 lasing positions, approximately 12 cc of tissue will be vaporized with minimal coagulation of tissue.

Lower power, for example 30 watts of Holmium:YAG laser energy (2 joules per pulse at a repetition rate of 15 pulses per second) may be employed for about 30 seconds to about 1 minute at each lasing position, for example with the device inserted at 2, 4, 8, 10 o'clock for an average sized prostate, and at 6 or 5 and 7 o'clock if the median lobe is enlarged.

The devices of FIGS. 20–23 may be inserted to a depth of at least 0.5 cm into a lobe of the prostate and a similar amount of laser energy may be emitted. The procedure may then be repeated at about 1 cm intervals from the earlier puncture and lasing sites.

If a device of the present invention is used to vaporize a tumor, Excimer or holmium:YAG lasers are preferred. If it is desired to coagulate the tumor in situ, an argon, KTP, diode or Nd:YAG laser may be used.

The side firing devices of FIGS. 1–19 and FIG. 24 may be inserted into the center of the tumor if it is spherical, and energy may be emitted, for example, at a given level for the same amount of time at 3, 6, 9 and 12 o'clock. If the tumor is ovoid, energy may be emitted, for example at a given level of energy at 6 and 12 o'clock for 30 seconds, and at 3 and 9 o'clock for 15 seconds, producing an oval coagulation and/or vaporization zone. Alternatively, for an ovoid tumor, for example, a given level of energy may be emitted for the same amount of time at 2, 4, 8 and 10 o'clock. If the tumor is bean or crescent shaped, the device may be inserted at two or more points and fired, for example, at a given amount of energy for the same or a different amount of time in directions necessary to assure complete coagulation or vaporization of the tumor.

If the tumor adjoins a vital blood vessel, duct, nerve or other structure, the device may be inserted between the blood vessel, duct, nerve or structure and fired away therefrom in one or more directions. In any case, if a shallower depth of vaporization or coagulation is desired, the amount of energy and/or the amount of time may be varied.

Numerous variations and modifications of the embodiments described above may be effected without departing from the spirit and scope of the novel features of the invention. No limitation with respect to the specific apparatus illustrated herein is intended or should be inferred. The above description is, of course, intended to cover by the appended claims all such modifications as fall within the scope of the claims.

We claim:

1. A catheter device adapted for delivering laser energy to a body tissue comprising:
    a) an elongate hollow tube defining first and second spaced-apart ports;
    b) a flexible energy conduit adapted for connection to a laser energy source, extending through said tube and including a distal end adapted to emit laser energy to a predetermined tissue site and the distal end portion thereof defining a channel in said tube in fluid flow communication with said first and second ports respectively; and
    c) a fluid conduit for passing a fluid or creating a vacuum through said first and second ports and through said channel for cooling said distal end portion and cleaning said distal end of said energy conduit;
    wherein said first and second ports in said tube define fluid inlet and outlet ports respectively and said conduit for passing a fluid comprises a fitting defining an interior cavity in fluid flow communication with a fluid source, said tube extending through said fitting; whereby said inlet port in said tube is located in fluid flow communication with said cavity in said fitting and the fluid flows through said channel and exits through said outlet port.

2. A catheter device adapted for delivering laser energy to a body tissue comprising:
    a) an elongate hollow tube defining first and second spaced-apart ports;
    b) a flexible energy conduit adapted for connection to a laser energy source, extending through said tube and including a distal end adapted to emit laser energy to a predetermined tissue site and the distal end portion thereof defining a channel in said tube in fluid flow communication with said first and second ports respectively; and
    c) a fluid conduit for passing a fluid or creating a vacuum through said first and second ports and through said channel for cooling said distal end portion and cleaning said distal end of said energy conduit;
    wherein said first and second ports in said tube comprise fluid inlet and outlet ports respectively and said fluid conduit for passing a fluid includes a handpiece defining an interior cavity in fluid flow communication with a source of fluid, said tube extending into said handpiece; whereby said inlet port in said tube is located in fluid flow communication with said interior cavity and fluid flows through said channel and exits through said outlet port.

3. A catheter device adapted for delivering laser energy to a body tissue comprising:
    a) an elongate hollow tube defining first and second spaced-apart ports;
    b) a flexible energy conduit adapted for connection to a laser energy source, extending through said tube and including a distal end adapted to emit laser energy to a predetermined tissue site and the distal end portion thereof defining a channel in said tube in fluid flow communication with said first and second ports respectively; and
    c) a fluid conduit for passing a fluid or creating a vacuum through said first and second ports and through said channel for cooling said distal end portion and cleaning said distal end of said energy conduit;
    wherein said fluid conduit for creating a vacuum comprises a fitting defining an interior cavity in fluid flow communication with a vacuum source, said tube extending into said fitting; whereby said first port in said tube is located in fluid flow communication with said cavity in said fitting and said fluid flows successively through said second port, said channel and then through said first port in response to the creation of a vacuum in said tube.

4. A catheter device adapted for delivering laser energy to a body tissue comprising:
   a) an elongate hollow tube defining first and second spaced-apart ports;
   b) a flexible energy conduit adapted for connection to a laser energy source, extending through said tube and including a distal end adapted to emit laser energy to a predetermined tissue site and the distal end portion thereof defining a channel in said tube in fluid flow communication with said first and second ports respectively; and
   c) a fluid conduit for passing a fluid or creating a vacuum through said first and second ports and through said channel for cooling said distal end portion and cleaning said distal end of said energy conduit;
   wherein said fluid conduit for creating a vacuum comprises a handpiece defining an interior cavity in fluid flow communication with a vacuum source, said tube extending into said handpiece whereby said first port in said tube is located in fluid flow communication with said cavity in said handpiece and fluid is guided successively through said second port and said channel and then through said first port in response to the vacuum in said tube.

5. A catheter device adapted for delivering laser energy to a body tissue comprising:
   a) an elongate hollow tube defining first and second spaced-apart ports;
   b) a flexible energy conduit adapted for connection to a laser energy source, extending through said tube and including a distal end adapted to emit laser energy to a predetermined tissue site and the distal end portion thereof defining a channel in said tube in fluid flow communication with said first and second ports respectively; and
   c) a fluid conduit for passing a fluid or creating a vacuum through said first and second ports and through said channel for cooling said distal end portion and cleaning said distal end of said energy conduit;
   wherein said first and second ports in said tube define fluid inlet and outlet ports respectively, said fluid conduit for passing a fluid comprising a handpiece defining an interior cavity in fluid flow communication with a fluid source and said tube extends into said handpiece and said fluid inlet port thereof is in fluid flow communication with said cavity in said handpiece, said fluid conduit for creating a vacuum comprising a fitting including an interior cavity in fluid flow communication with a vacuum source, said tube extending into said fitting and said fluid outlet port being in fluid flow communication with said cavity in said fitting whereby fluid is guided successively through said inlet port in said tube and said channel and then through said outlet port in said tube in response to the introduction of fluid through said inlet port and the vacuum through said outlet port.

6. A catheter device adapted for delivering laser energy to a body tissue comprising:
   a) an elongate hollow tube defining first and second spaced-apart ports;
   b) a flexible energy conduit adapted for connection to a laser energy source, extending through said tube and including a distal end adapted to emit laser energy to a predetermined tissue site and the distal end portion thereof defining a channel in said tube in fluid flow communication with said first and second ports respectively; and
   c) a fluid conduit for passing a fluid or creating a vacuum through said first and second ports and through said channel for cooling said distal end portion and cleaning said distal end of said energy conduit;
   wherein each said tube and said energy conduit includes opposed side surfaces and said opposed side surfaces of said tube are crimped respectively against said opposed side surfaces of said energy conduit to define a first upper passage and a second lower passage in said tube together defining said channel in said tube.

7. A catheter device adapted for delivering laser energy to a body tissue comprising:
   a) an elongate hollow tube including a closed distal end and a distal peripheral end portion defining a port;
   b) an energy conduit extending longitudinally through said tube including a distal end spaced from and parallel to said port and adapted to emit laser energy; and
   c) means for directing the laser energy emitted from said distal end of said energy conduit outwardly through said port in said tube in a direction generally perpendicular to the longitudinal axis of said tube and said energy conduit;
   wherein said tube includes a peripheral wall defining first and second ports therein defining fluid inlet and outlet ports respectively and said conduit is spaced from said wall to define a fluid channel in said tube, said device further comprising a fitting in fluid flow communication with a source of fluid and adapted for connection to said first port whereby fluid is adapted to flow through said channel and exit through said second port in said tube.

8. A catheter device adapted for delivering laser energy to a body tissue comprising:
   a) an elongate hollow tube including a closed distal end and a distal peripheral end portion defining a port;
   b) an energy conduit extending longitudinally through said tube including a distal end spaced from and parallel to said port and adapted to emit laser energy; and
   c) means for directing the laser energy emitted from said distal end of said energy conduit outwardly through said port in said tube in a direction generally perpendicular to the longitudinal axis of said tube and said energy conduit;
   wherein said tube includes a peripheral wall defining first and second ports therein defining fluid inlet and outlet ports respectively and said conduit is spaced from said wall to define a fluid channel in said tube, said device further comprising a handpiece defining an interior cavity in fluid flow communication with a source of fluid, said tube extending into said cavity of said handpiece such that said inlet port in said tube is located in fluid flow communication with said cavity whereby said fluid is adapted to flow through said inlet port and said channel and exits through said outlet port in said tube.

9. A catheter device adapted for delivering laser energy to a body tissue comprising:
   a) an elongate hollow tube including a closed distal end and a distal peripheral end portion defining a port;
   b) an energy conduit extending longitudinally through said tube including a distal end spaced from and parallel to said port and adapted to emit laser energy; and c) means for directing the laser energy emitted from said distal end of said energy conduit outwardly through said port in said tube in a direction generally perpendicular to the longitudinal axis of said tube and said energy conduit;

wherein said tube includes a peripheral wall defining first and second ports and said conduit is spaced from said wall to define a fluid channel in said tube, said device further comprising a fitting in fluid flow communication with a vacuum source and adapted for connection to said first port; whereby fluid is adapted to flow successively through said second port; said channel and then through said first port in response to the creation of a vacuum in said tube.

10. A catheter device adapted for delivering laser energy to a body tissue comprising:

a) an elongate hollow tube including a closed distal end and a distal peripheral end portion defining a port;

b) an energy conduit extending longitudinally through said tube including a distal end spaced from and parallel to said port and adapted to emit laser energy; and c) means for directing the laser energy emitted from said distal end of said energy conduit outwardly through said port in said tube in a direction generally perpendicular to the longitudinal axis of said tube and said energy conduit;

wherein each said tube and said energy conduit includes opposed side surfaces and said opposed side surfaces of said tube are crimped respectively against said opposed side surfaces of said energy conduit to define a first upper and a second lower passageway in said tube together defining a channel in said tube in fluid flow communication with respective inlet and outlet ports formed in said tube.

11. A catheter device adapted for delivering laser energy to a body tissue comprising:

a) an elongate hollow tube including a closed distal end and a distal peripheral end portion defining a port;

b) an energy conduit extending longitudinally through said tube including a distal end spaced from and parallel to said port and adapted to emit laser energy; and c) means for directing the laser energy emitted from said distal end of said energy conduit outwardly through said port in said tube in a direction generally perpendicular to the longitudinal axis of said tube and said energy conduit;

wherein said distal end of said conduit is covered by a capillary tube including a closed distal end.

12. A catheter device adapted for delivering laser energy to a body tissue comprising:

a) a laser energy source;

b) an elongate hollow tube defining first and second spaced-apart ports;

c) a flexible energy conduit extending through said tube and including a proximal end adapted for connection to the laser energy source and a distal end adapted to emit laser energy to a predetermined tissue site, the distal end portion thereof defining a channel in said tube in fluid flow communication with said first and second ports respectively; and d) a fluid conduit for passing a fluid or creating a vacuum through said first and second ports and through said channel for cooling said distal end portion and cleaning said distal end of said energy conduit;

wherein said first and second ports in said tube define fluid inlet and outlet ports respectively and said fluid conduit for passing a fluid comprises a fitting defining an interior cavity in fluid flow communication with a fluid source, said tube extending through said fitting; whereby said inlet port in said tube is located in fluid flow communication with said cavity in said fitting and the fluid flows through said channel and exits through said outlet port.

13. A catheter device adapted for delivering laser energy to a body tissue comprising:

a) a laser energy source;

b) an elongate hollow tube defining first and second spaced-apart ports;

a flexible energy conduit extending through said tube and including a proximal end adapted for connection to the laser energy source and a distal end adapted to emit laser energy to a predetermined tissue site, the distal end portion thereof defining a channel in said tube in fluid flow communication with said first and second ports respectively; and d) a fluid conduit for passing a fluid or creating a vacuum through said first and second ports and through said channel for cooling said distal end portion and cleaning said distal end of said energy conduit;

wherein said first and second ports in said tube comprise fluid inlet and outlet ports respectively and said fluid conduit for passing a fluid includes a handpiece defining an interior cavity in fluid flow communication with a source of fluid, said tube extending into said handpiece; whereby said inlet port in said tube is located in fluid flow communication with said interior cavity and fluid flows through said channel and exits through said outlet port.

14. The catheter device of claim 13 wherein the laser energy source is selected from the group consisting of an argon laser, a KTP laser, a Nd:YAG laser, a diode laser, an Alexandrite laser, and a holmium: YAG laser.

15. The catheter device of claim 13 wherein the laser energy source is a holmiumYAG laser.

* * * * *